United States Patent
Dietrich et al.

(10) Patent No.: US 8,506,469 B2
(45) Date of Patent: *Aug. 13, 2013

(54) METHOD TO ENHANCE NEURAL TISSUE OPERATION

(75) Inventors: Stefan Dietrich, Erlangen (DE); Christoph Beck, Bubenreuth (DE)

(73) Assignee: Cerbomed GmbH, Erlangen (DE)

(*) Notice: Subject to any disclaimer, the term of this patent is extended or adjusted under 35 U.S.C. 154(b) by 1009 days.

This patent is subject to a terminal disclaimer.

(21) Appl. No.: 12/465,209

(22) Filed: May 13, 2009

(65) Prior Publication Data
US 2009/0287035 A1 Nov. 19, 2009

Related U.S. Application Data

(60) Provisional application No. 61/052,705, filed on May 13, 2008.

(51) Int. Cl.
*A61N 2/00* (2006.01)

(52) U.S. Cl.
USPC ............................................. 600/9

(58) Field of Classification Search
USPC ... 600/9–15, 545; 128/897–898; 607/45–46, 607/55
See application file for complete search history.

(56) References Cited

U.S. PATENT DOCUMENTS

| | | | | |
|---|---|---|---|---|
| 4,267,838 A * | 5/1981 | McCall | ........................ | 606/204 |
| 4,319,584 A * | 3/1982 | McCall | ........................ | 607/136 |
| 7,601,115 B2 * | 10/2009 | Riehl | ............................. | 600/14 |
| 7,797,042 B2 * | 9/2010 | Dietrich et al. | ................... | 607/2 |
| 2003/0130706 A1 * | 7/2003 | Sheffield et al. | ............... | 607/46 |
| 2003/0195588 A1 * | 10/2003 | Fischell et al. | ................. | 607/55 |
| 2011/0046432 A1 * | 2/2011 | Simon et al. | .................... | 600/14 |

FOREIGN PATENT DOCUMENTS
DE   2005003735 A1 *  7/2006

* cited by examiner

*Primary Examiner* — John Lacyk
(74) *Attorney, Agent, or Firm* — Lucas & Mercanti, LLP

(57) ABSTRACT

The invention relates to a method for modulation, augmentation and/or stimulation of neural tissue and/or neural tissue related functionality with stimulating neural tissue and/or neural tissue related functionality with stimuli by which neural activity related local perfusion changes, electro-neurochemical, biochemical, neural modulative or neuroplastical responses and/or alterations in 'metabolism supply lines-neural tissue' interaction processes in vertebrates can be triggered and/or influenced.

19 Claims, 8 Drawing Sheets fMRI stimulation and BrainVoyager® QX evaluation protocol.

METHOD TO ENHANCE NEURAL TISSUE OPERATION

FIELD OF INVENTION

The present invention generally relates to the fields of neuroenhancement, neurostimulation and neuralmodulation and to implantable, minimally-invasive and non-invasive medical and holistic devices capable to modulate, augmentate and/or stimulate neural tissue and/or neural tissue related functionality by triggering and/or influencing neural activity and uses thereof.

BACKGROUND

The last decades have produced new exciting and emerging technologies to help neurostimulation systems gaining fast-growing clinical as well as patient acceptance. Neurostimulation systems are currently employed to treat numerous debilitating diseases, including: pain, neurological and movement disorders like Parkinson's disease, epilepsy or tremor, cardiovascular, cerebrovascular or respiratory disorders, bladder, bowel and sexual disorders, psychiatric disorders like major depression or obsessive compulsive disorders, hearing and visual disorders. Pre-market approvals have been granted for further systems to explore several other applications. All these systems establish the possibility that the future focus is not just on treating people with neurological and neuropsychiatric diseases, meaning 'restoring' them to human typical functioning and operation, but that neuro-enhancement can a) maintain restored status and b) super-improve natural functioning and operation of vertebrates neural tissue and/or neural tissue related functionality by triggering and/or influencing neural activity.

When having suffered from a neurological or neuropsychiatric disease, this normally means having lost the economical-competitive and emotional-competitive link to the patient's social competitors, for example in business, education and social life.

This in mind, a thorough rehabilitation process should lead to competitive advantages. These will not result from just typical restoring. Patients need methods and devices to regain their lost time.

Furthermore, many people have to face unfavorable predeterminations—social or genetically, for example diseases or inadequate access to education. It is important for them to boost their mental preparation to be competitive.

SUMMARY OF THE INVENTION

The invention disclosed and claimed herein addresses problems noted above. The present invention is a method to modulate, augmentate and/or stimulate neural tissue and/or neural tissue related functionalities for enhancing their present operation.

This invention is based, in part, on our discovery that acute orthodromic transdermal electrical stimulation of parasympathetic afferent nerve fibers at the human pinna leads to positive blood oxygenation level-dependent responses in significant parts of the human brain associated with higher order relay nuclei of vagal afferent pathways, limbic system as well as senso-motoric areas measured by functional magnetic resonance imaging. In an active_to_baseline comparison, significant areas of activation were detected in the brainstem, more precisely the left locus coeruleus/the pontine tegmentum, the thalamus (left>right)/anterior and medial thalamic nuclei/Ncl. paraventricularis, the posterior part of the putamen, the left prefrontal/superior-frontal cortex, bilateral post-central gyrus, the left posterior cingulated gyrus and the left insula. Deactivations were found in the nucleus accumbens and the right cerebellar hemisphere. Thus, it has been discovered that the present operation of neural parasympathetic tissue and related structures can be enhanced by a transdermal applied stimulus due to neural activity related local perfusion changes, electro-neuro-chemical, biochemical or neuroplastical responses and/or alterations in 'metabolism supply lines-neural tissue' interaction processes in vertebrates.

In one embodiment, the present invention may be used for enhancing the performance of previously mentioned neuronal structures and related pathways in vertebrates. The method comprises stimulation, in particular transdermal stimulation, of afferent parasympathetic nerves, for example the vagus nerve, its roots or parts of it, using biophysical, electrical, electrochemical, electromagnetical, neurochemical, sound, radition impulses and/or waves. Applying the method to a vertebrate aims at enhancing its cognitive and emotional abilities or psychophysiologically influenced parameters, for example its heart rate variability or sleep quality.

The stimulation may be achieved by any physiologically adequate or inadequate stimulus (e.g. biophysical, electrical, electrochemical, electromagnetical, neurochemical, sound, radition impulses and/or waves) suitable for stimulation the neural structures, preferably by simple or complex electrical stimuli or signal patterns. When using an electrical stimuli, the signals may be either unipolar or bipolar, typically in a range of 0.01 volts up to 100 volts, depending on the application area and other factors. In order to control the electrical stimulus energy an open loop control or closed loop control may be applied. The stimulus source may be designed as a voltage driven voltage source, or a current driven voltage source, or a voltage driven current source, or a current driven current source. The preferable frequency range for repetitive stimulation, measured at the electrodes, is from 0.01 hertz to 1000 hertz. The on-time of each electrical stimulus may typically range from 1 µs to 10 s. Preferably all stimulus parameters are precisely adjustable in steps smaller than 1%.

The present invention may comprise the following aspects:

Modulating, augmentating and/or stimulating neural tissue and/or neural tissue related functionality can be achieved by a method according to the present invention. In this method, neural activity related local perfusion changes, electro-neuro-chemical, biochemical or neuroplastical responses and/or alterations in 'metabolism supply lines-neural tissue' interaction processes in vertebrates are triggered and/or influenced by means of stimulating neural tissue and/or neural tissue related functionality with stimulating signals.

At least one means of modulation, augmentation and/or stimulation capable to interact with neural tissue or neural tissue related biological structures is positioned in contact with or proximate to said neural tissue or neural tissue related biological structures. Stimuli are supplied to at least one means of modulation, augmentation and/or stimulation capable to directly or indirectly interact with a proximate axonal nerve system related target.

By means of said stimulation it is possible to generate local neurophysiological, neurovascular, neuroendocrine or neuro-biochemical information capable to trigger effects in the brainstem, subcortical and/or cortical areas for the purpose of enhancing the performance of neuronal structures and related pathways in vertebrates leading to improved cognitive and emotional abilities or for treating neurological and/or neuropsychiatric disorders and/or symptoms resulting from underlying causes.

The stimulating signals can be biophysical, electrical, electrochemical, electromagnetical, neurochemical, sound, radition impulses and/or waves, wherein the signal amplitude and the signal frequency can be modulated.

The method may be used with one or more vertebrates, each suitable to modulate, augmentate and/or stimulate their neural tissue and/or neural tissue related functionality and/or exhibiting one or more common specific neurological and/or neuropsychiatric disorders.

Said means of modulation, augmentation and/or stimulation can be positioned in contact with or proximate to a nerve of a vertebrate, wherein said nerve may comprise parasympathetic and/or sympathetic fibers. In particular, the Nervus vagus, the ramus auricularis nervi vagi, and/or a trigeminal nerve may be stimulated. The ramus auricularis nervi vagi may be stimulated at the pinna and/or the external auditory canal.

Said stimulation may generate unidirectionally propagating action potentials.

Said parasympathetic nerve fibers can be afferent or efferent.

Modulation, augmentation and/or stimulation by means of a method according to the present invention may lead to positive blood oxygenation level-dependent responses in the central nerve system and/or the brain of a vertebrate, wherein said responses take place in the left locus coeruleus and/or the pontine tegmentum and/or the thalamus (left>right) and/or anterior and medial thalamic nuclei and/or the Hippocampus and/or Ncl. Paraventricularis and/or the posterior part of the putamen and/or the left prefrontal and/or superior-frontal cortex and/or bilateral postcentral gyrus and/or the left posterior cingulated gyrus and/or the left insula and/or nucleus accumbens and/or the right cerebellar hemisphere.

The method according to the present invention may in particular be used with neurological and/or neuropsychiatric disorder and/or symptoms resulting from underlying cause selected from a group consisting of Alzheimer disease, Parkinson disease, Tremor, major depression, bipolar disorders, anxiety, eating disorders, sleep disorders, pain, tinnitus, cardio-vascular disorders, artrial fibrillation, epilepsy, schizophrenia, addictive disorders, dementia, attention deficit disorders, premenstrual syndrome, obesity, spasticity, tourette syndrome, dystonia, neurogenic and psychogenic bladder disorders, neurogenic and psychogenic defecation disorders, neurogenic and psychogenic sexual disorders, obsessive compulsive disorders.

Enhanced cognitive and emotional abilities can be enhancement of productivity, attention, learning, concentration, awareness, vigilation, tranquillization, sedation, emotional assessment, valuation, emotional intelligence, decisive abilities, retentiveness, conversation.

Stimulation can be provided by means of implanted neurostimulators, including vagus nerve stimulators, deep brain stimulators or cortical stimulators. Stimulation can also be provided by minimally invasive stimulators. Stimulation can also be provided by non-invasive neurostimulators, including transcutaneous vagus nerve stimulators or transcranial magnetic stimulators.

For stimulation a stimulation pulse with at least one of a plateau pulse width of adjustable duration, a rising and decaying trailing phase of adjustable duration and a charge recovery phase of adjustable duration can be used. The stimulation characteristic can be mirrored.

Said means of modulation, augmentation and/or stimulation may comprise at least one stimulation electrode.

The invention also relates to a method of generating blood oxygenation level-dependent responses in higher order relay nuclei of vagal afferent pathways, wherein the method may comprises one or more of the following steps:

generating propagating action potentials of the Ramus auricularis nervi vagi by means of stimulation configuring said propagating action potentials to pass through the canaliculus mastoideus configuring said propagating action potentials to pass the Ganglion rostrale configuring said propagating action potentials to generate blood oxygenation level-dependent responses in the brainstem configuring said propagating action potentials to generate blood oxygenation level-dependent responses in the Thalamus.

Said method of generating blood oxygenation level-dependent responses in higher order relay nuclei of vagal afferent pathways may furthermore comprise means of influencing propagation of said action potentials towards subcortical and cortical brain areas associated with vagal and limbic pathways.

DETAILED DESCRIPTION OF THE INVENTION

The following description for carrying out the invention is not to be taken in a limiting sense, but is made merely for the purpose of describing the general principles of the invention.

An illustrative embodiment of a device according to the present invention is shown in the drawing, in which.

The stimulation device of this embodiment is designated and suitable for transdermal stimulation of the vagus nerve in the area of the external auditory canal and/or the auricle by stimulation electrodes insertable into the external auditory canal.

Figure 1:
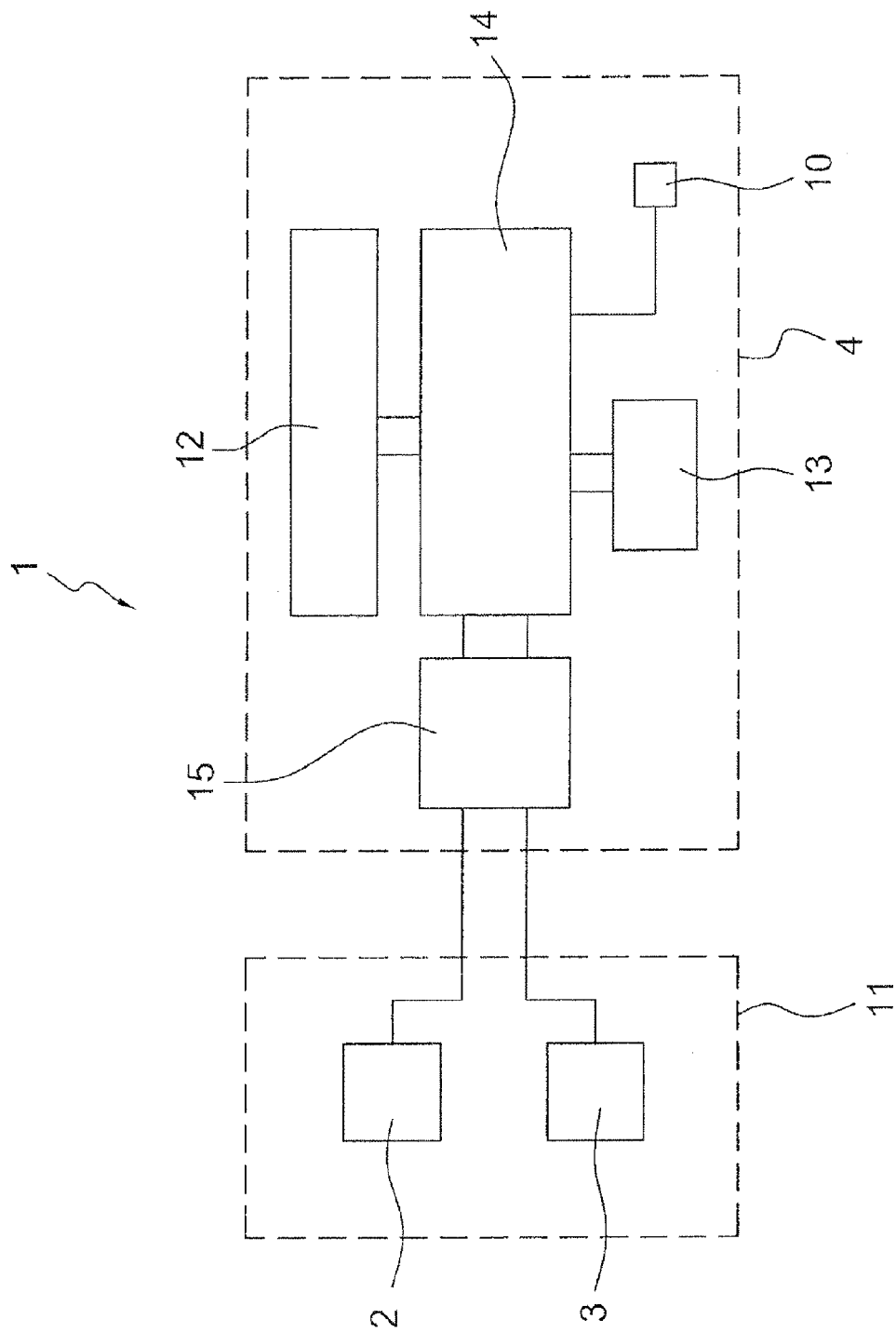
FIG. 1 is a schematic circuit diagram of a device for transdermal stimulation of the auricular branch of the vagus nerve.

The circuit diagram of a device 1 for transdermal stimulation of the vagus nerve is shown schematically in FIG. 1. The auricular branch in particular is stimulated in order to influence psychovegetative parameters. In this way, for example, stress levels can be reduced, or a positive influence can be exerted on depressions or other neuropsychiatric disturbances.

The device 1 is composed principally of the stimulation electrode unit 11 (indicated with broken lines on the left-hand side of FIG. 1) and of the control unit 4 (indicated with broken lines on the right-hand side of FIG. 1).

The stimulation of the nerve takes place via the stimulation electrode 2. The reference electrode 3 serves as an electrical reference point. Both electrodes 2, 3 form the stimulation electrode unit 11. Electrodes 2 and 3 for transdermal stimulation are known, commercially available and easy to produce.

The stimulation frequency and the stimulation strength are predetermined and generated by the control unit 4. These parameters are set by various control elements 12. Oscillating signals are needed for transdermal stimulation. They are generated by an oscillator 13 located in the control unit 4. The input and output signals that are delivered via an input/output circuit 15 of the stimulation electrode unit 11 are processed in a logic and control circuit 14. The current is supplied from a battery 10.

Figure 2:
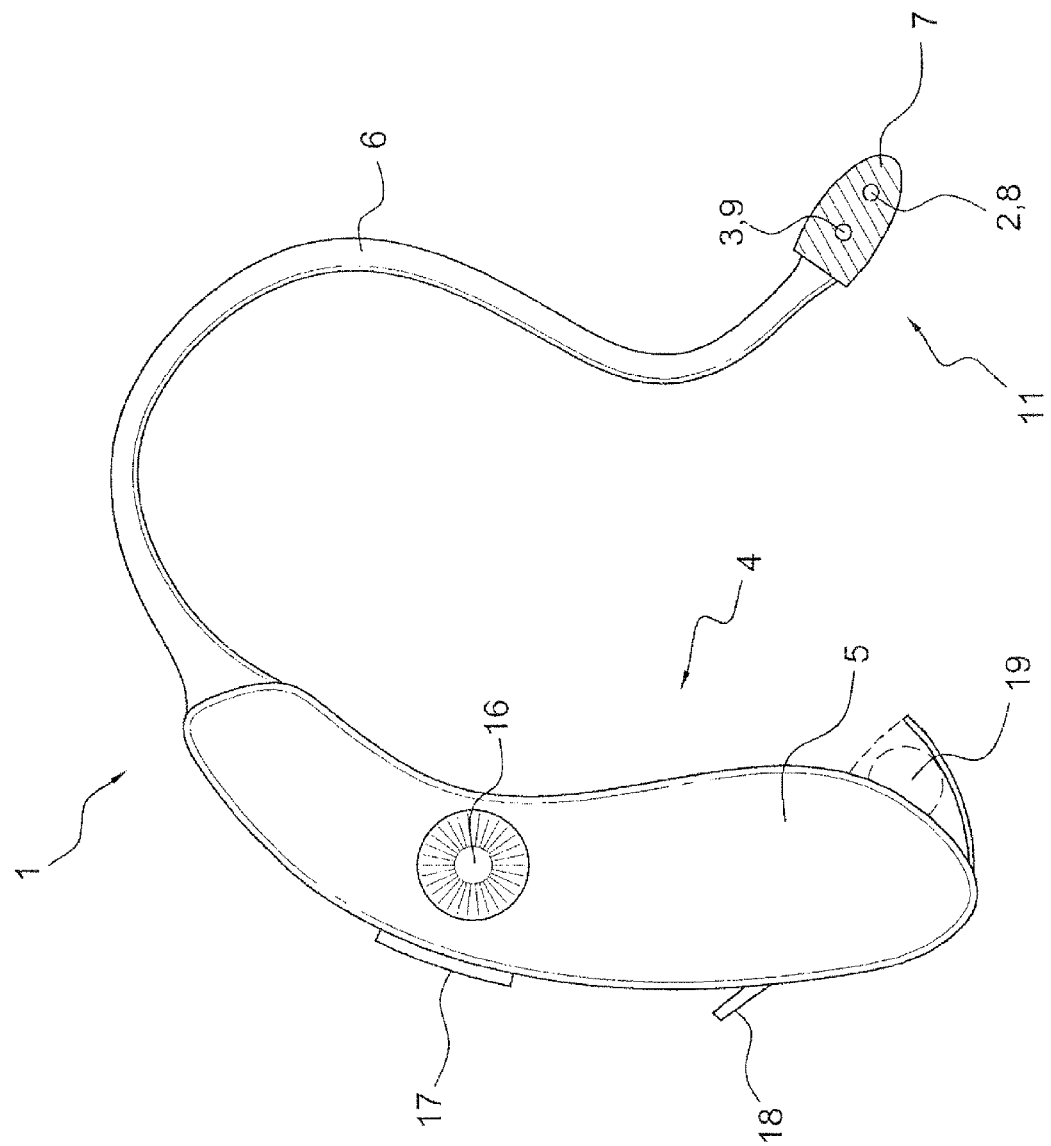
FIG. 2 shows the stimulation device, designed as a behind-the-ear device.

As can be seen from FIG. 2, the device 1 is similar in structure to a behind-the-ear hearing aid and has a housing 5. The stimulation electrode unit in the form of an electrode head or an ear electrode 7 is inserted into the external auditory canal, such that the stimulation electrode 2 and the reference electrode 3 come to lie on the skin surface. The connection between the electrode head 7 and the part of the housing 5 shown on the left-hand side of FIG. 2 is designed as a bow-shaped extension piece 6, through which all the input and output lines between stimulation electrode unit and control unit are also routed; the bow-shaped extension piece 6 is fitted over the upper margin of the auricle. At the end of the connection or link, the control unit 4 is located in the housing 5 with an approximate size of 5 cm×2 cm×1 cm.

Integrated into the control unit 4 there is, in the first instance, a stimulation strength regulator 16 for regulating the amplitude (strength) of the stimulation signal. High amplitudes stimulate the nerve more than low amplitudes. Moreover, the required stimulation strength varies between individuals.

The control unit 4 also contains a stimulation frequency regulator 17 for regulating the frequency pattern of the stimulation signal. Thus, signals following one another in rapid succession can be controlled just as can signals that follow one another at a greater interval.

An on/off switch 18 is also provided for activating and deactivating the device 1. A battery compartment 19 is used to accommodate a small button-cell battery, preferably of size 13 to 675.

One example of the action of the proposed device on the vagus nerve is the following: The applied current is between 0.25 and 1.5 mA. The frequency of the current is between 20 and 30 Hz. The pulse width is between 250 and 500 ms. The current is applied every 3 to 5 minutes for ca. 30 seconds.

The proposed stimulation device 1 is very small and is therefore eminently suitable for home use. It affords the wearer great freedom, because its placement behind the ear is very advantageous and discrete.

The stimulation and reference electrodes 2, 3 must have electrical contact with the surface of the patient's skin, and this contact is permitted by contact points 8, 9 which can be designed as small metal balls. The electrodes 2, 3 lie on the inner face of the tragus, i.e. an anatomical part of the auricle. The distance between the contact points 8, 9 is preferably between 1 mm and 15 mm, particularly preferably between 2 mm and 6 mm.

In another variant of the solution, the earpiece can be inserted farther into the auditory canal and can there also provide stimulation of the vagus nerve. For this purpose, the electrodes 2, 3 can be designed as flat surface electrodes, for example. Further nerve endings of the vagus nerve are stimulated deeper within the auditory canal.

The electrodes 2, 3 are connected to cables (not shown) which are routed in a concealed manner within the earpiece. The cable connections in turn are connected to the control unit 4 preferably located behind the ear. The connection is established via the bow-shaped extension piece 6, as has been explained. The stimulation frequency, stimulation strength, impulse duration, stimulation intervals and current form are set via the stimulation frequency regulator 17.

In a similar way to an in-the-ear hearing aid, the whole technology can also be integrated into a device that comes to lie in the concha of the ear and fills it.

The device is supplied with current by the battery 10 and is therefore independent of an external power source. Provision can be made for the current to be supplied via a rechargeable battery 10 which is integrated into the housing 5. For the recharging operation, the device 1 is inserted into a small specially designed case which is connected to an external power source and which charges the battery 10 overnight by induction, for example.

The earpiece can additionally be provided with a sensor for measuring the pulse and oxygen saturation. Such sensors are known for measurement of respiratory function and pulse and are commercially available. The measured values can be recorded on a memory chip located in the housing 5 behind or in the ear, such that they can later be read out by a physician via a cableless interface and can be evaluated using software. From the change in the pulse rate variability calculated by the software, the physician is able to obtain important information concerning the psychovegetative modulation effect of the stimulation device and is thus also provided with control data over the course of the therapy.

The described device can be constructed according to standard values, or the earpiece and other parts can be manufactured individually.

In an alternative embodiment, the electrode head 7 and the control unit 4 are stored separately and are connected via a cable.

In a further alternative, the stimulation technology can be integrated into a mobile telephone and into its hands-free unit. The control unit 4 and its electronics can in this case be integrated into the circuitry of the mobile telephone. The stimulation unit 7 with stimulation electrode 2 and reference electrode 3 can be installed in the earpiece of the hands-free unit. The communication between earpiece and mobile telephone can be wireless, for example by means of Bluetooth technology, or can be via a connecting cable.

It is also possible for the technology to be integrated into headphones and devices for example for digital media playback. These can be MP3 players or, in particular, MD players or Discmans.

FIG. 3 is divided in four sections, where section A shows the application site of the electrode. The stimulation electrode is placed at the tragus of the left pinna. In section B it is shown, that the bipolar stimulation electrode is made of silver and placed on an acrylic body for a comfortable fit in the pinna. According to section C, for fMRI stimulation, the tVNS stimulator is placed outside the scanner room and connected to the electrodes by an MR compatible cable. Referring to the section D, the stimulus was a modified monophasic rectangle impulse with a pulse width of 250 µs and the amplitude varied between 4 and 8 mA.

EXAMPLE

Introduction

Current state-of-the-art vagus nerve stimulation (VNS) comprises an implantable device, called the Neuro-Cybernetic prosthesis (NCP_) (Cyberonics Inc., Houston, Tex., USA) w33x. It has shown to have beneficial clinical effects in treating epilepsy w3, 36x and recently promising results in treating patients with therapy-refractory depression w20, 22, 28, 29x. At present, VNS requires a surgical intervention for implanting the stimulation unit in the chest and connecting an electrode array wrapped around the left cervical vagus nerve branch in the neck. The array delivers electrical current with variable parameters, such as amplitude, pulse width, frequency and on-time/off-time ratio, to the nerve with the objective of beneficially influencing brain areas involved in the onset of epilepsy or depression. Although promising, the current implantable device has numerous disadvantages, namely high costs, the requirement of a clinical infrastructure for surgical intervention, surgical risks, an irreversible surgical procedure, a risk of nerve injuries and voice alterations when the device is activated. Furthermore, long-term effects of this method are not known. This in mind, a non-invasive method to stimulate the vagus nerve would have substantial benefits for neurological and neuropsychiatric patients. In 2000, Ventureyra w35x proposed a non-invasive concept by stimulating the Ramsey Hunt zone in the pinna, a delimited skin area supplied by the ganglion geniculi of the nervus intermedius. It was suggested that stimuli could reach the vagus nerve and the nucleus of the solitary tract via the intermediary nerve of Wrisberg, a branch of the facial nerve. Faligatter et al. w6, 7x and Polak et al. w25x further investigated the possibility of stimulating cutaneous representations of the vagus nerve in the external auditory canal including the inner side of the tragus using established techniques of early acoustic evoked potentials for use as a diagnostic tool for Alzheimer's disease and Parkinson's disease. The assumption that direct transcutaneous VNS (tVNS) at the external ear is possible is reasoned from interpreting functional anatomy. The auricular branch of the vagus nerve (ramus auricularis nervi vagi) transverses the canaliculus mastoideus and the fissura petrotympanica and is distributed to the inner side of the pinna and the external auditory canal. Irritations of this nerve are mainly responsible for vegetative reactions, such as cough reflex and nausea w12, 32x. The functional neurobiology of how VNS-invasive or non-invasive-works is poorly understood. Several groups have used positron emission tomography w4, 8, 10, 11, 14x, single photon emission computed tomography w27, 34, 37, 39x or blood oxygen level dependent functional magnetic resonance imaging (BOLD fMRI) w2, 16, 17, 21, 23, 24, 31x to study VNS brain effects using the implantable NCP_. The literature appears inconsistent due to questionable methodologies, findings and conclusions. Overall, however, VNS causes acute and long-term changes in brain areas ascribed to the vagus nerve system and involved in the onset of neuropsychiatric disorders. To date, only one fMRI study has been performed to assess acute effects when undergoing tVNS in the human external canal w13x. This experiment was performed using a device designed and approved for the stimulation of neuromuscular tissue. The characteristics of this stimulation were a pulse width of 20 ms and a frequency of 8 Hz. Unfortunately, no information on the chosen shape of impulse (whether symmetric or asymmetric) was reported. The main difference between neuromuscular stimulation and neural tissue stimulation, however, are the parameters of the output signal. Our interpretation of the psychophysical research and literature shows that tVNS at the inner side of the tragus (parasympathetic stimulation) requires even more specific stimulation parameters. As an example, Lomarev et al. w17x have reported that VNS at 20 Hz resulted in significant brain activations, while at 5 Hz stimulation no significant difference was reached compared to baseline. The authors concluded that the activity of VNS is frequency-dependent in favour towards 20 Hz. Current literature supports these results w38x. Low-frequency stimulation between 0.5 and 10 Hz activates the sympathetic system, whilst 20-25 Hz is more suitable for parasympathetic nerve activation. Changing the pulse width towards 200-500 ms is therefore reasonable. Last but not least, we believe that using devices suitable for neuromuscular stimulation rather leads to unpleasant skin sensations that again will activate pain pathways and the sympathetic system. The objective of this study was to assess the effects of new parameter settings provided by a novel tVNS device using BOLD fMRI. This study contributes to the field, because it is both a feasibility and mode-of-action study of tVNS in healthy subjects.

Materials and Methods

Subjects

A total of four healthy male volunteers (aged 26-32 years) took part in this study. The participants had a mean age of 30 ("2.7) years. An itemised questionnaire was used to gain general anamnesis information. No volunteer ever had a clinical diagnosis of epilepsy, depression or neurofunctional disorders or had undergone associated therapy treatment in the past or indeed during the study. In a training session, all subjects were familiarised with the stimulation procedure. All subjects reported that they were used to the stimulus amplitude after a few seconds and so the current was lifted stepwise up to a level where a constant sensation was reached. The stimulation was always kept below a pain threshold (between 4 and 8 mA). The stimulation algorithm (see section below) was performed as in the later fMRI session. For this procedure, the subjects lay horizontally on an examination couch. Blood pressure and heart rate were recorded continuously during the training session (using PowerLab_4/25T and Chart_Software, AD Instruments, Spechbach, Germany). Laser Doppler flowmetry was performed at the finger pad of the left index to measure peripheral skin blood flow (OxyFlo XP Probe, Oxford Optronix Ltd., UK).

Figure 3C:
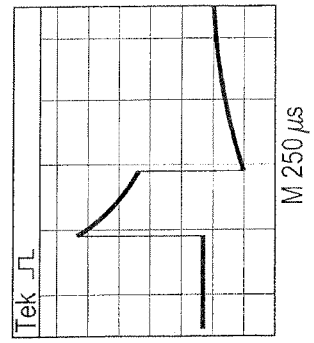
FIG. 3 shows the method and tVNS stimulator design.
Figure 3D:
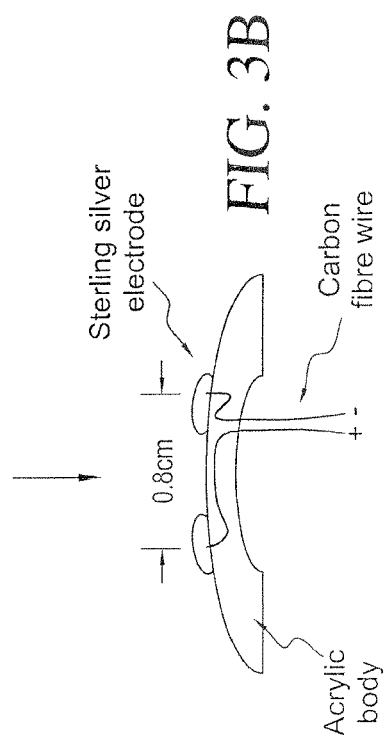
Figure 3A:
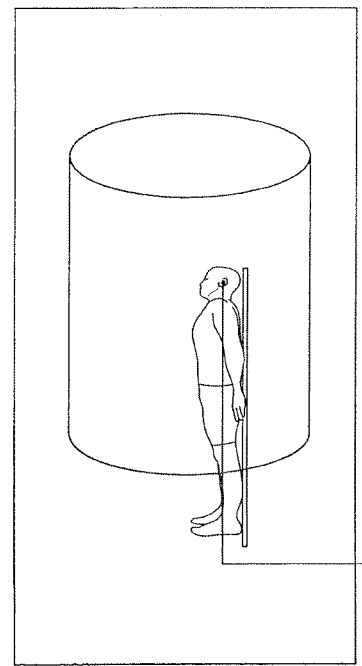
Figure 3B:
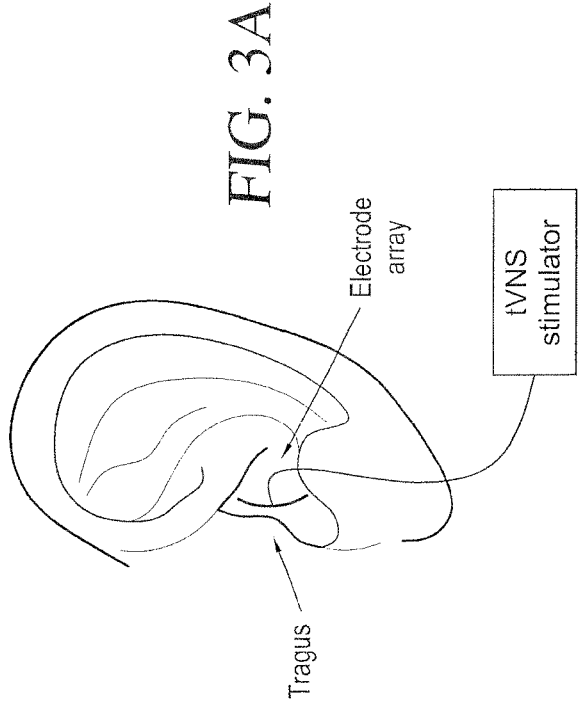

Stimulation Procedure tVNS was performed at the inner side of the left tragus (FIG. 3A) using a stand-alone electrical nerve stimulator connected with carbon fibre wires to an acrylic electrode array housing a sterling silver stimulation electrode and a reference electrode (FIG. 3B). The centre-to-centre distance of the surface electrodes was approximately 8 mm. The array was attached to the skin with an adhesive tape and ear canals were sealed by ear protection. All components of the electrode array and the connecting wires to the stimulator were manufactured without the use of any ferromagnetic components inside the scanner's magnetic field. The connecting wires were placed on the subject's chest along the longitudinal body axis. The tVNS stimulator was placed outside the scanner room (FIG. 3C). The stimulus was a monophasic-modified rectangle impulse (FIG. 3D) with a pulse width of 250 ms. Electrical current amplitude was varied individually between 4 and 8 mA. Individual adjustment of stimulation intensity was performed additionally before the scan. Stimulation frequency was kept at 25 Hz, which is known to activate parasympathetic nerve fibres w36x.

Experimental Protocol

Figure 4:
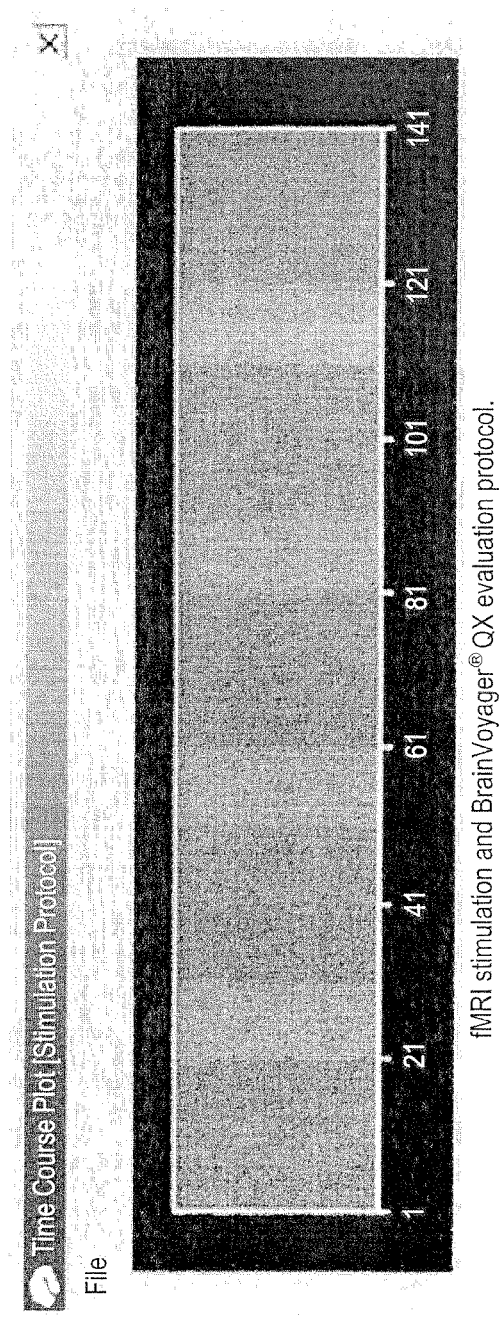
FIG. 4 shows a evaluation protocol.

Functional MRI sessions were performed using the following protocol: the experiment lasted 700 s and was started with a baseline lasting 100 s. This was followed by a first stimulation period of 50 s and a break/baseline of 100 s. Four alternating stimulation and baseline sequences were performed according to the scheme depicted in FIG. 4.

Magnetic Resonance Imaging

Functional MRI was performed with a 1.5-Tesla Avanto MRI scanner (Siemens Medical Solutions, Erlangen, Germany) at the Institute of Imaging and Therapy, Erlangen, Germany. The head of the subject was fixed in a head coil by rubber pads and both ears were plugged. A magnetisation prepared rapid gradient echo (MPRAGE) sequence was recorded consisting of 176 sagittal slices of 1-mm thickness and an inplane resolution of 256=256 pixel matrix (field of view: 224=224 mm2). Functional T2* weighted images were obtained using an echo planar imaging technique consisting of 36 axial slices (TRs110 ms, TEs60 ms, flip angles908, slice time of 5000 ms per block of 36 slices, slice thickness of 3 mm, field of view 224=224 mm2, 64=64 pixel). Possible head movements of the subject were corrected using the motion correction function of the SYNGO_scanner software (Siemens Medical Solutions).

Data Analysis and Statistics

Figure 5:
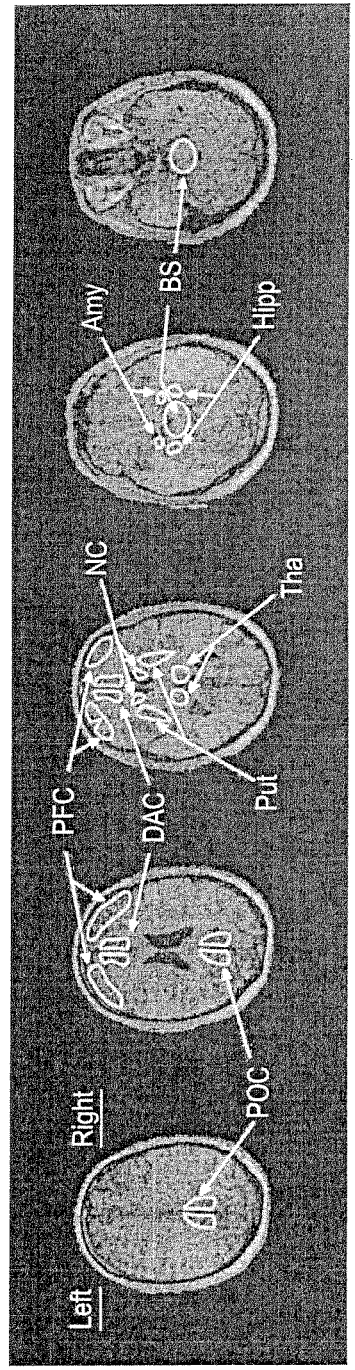
FIGS. 5 and 6 show cuts of the brain.

Psychophysical data were analysed with SCOPE_and CHART_(AD Instruments, Spechbach, Germany). Functional MRI post-processing was performed using BrainVoyager_QX (BrainInnovations, The Netherlands) with motion correction, temporal high-pass filter and linear trend removal. A general linear mode (GLM) for multistudies was used to detect activated brain areas. For displaying the activated clusters at different brain sites, the functional images were co-registered with the three-dimensional (3D) MPRAGE dataset using the routines according to the BrainVoyager_QX. Resulting transformations were merged to an overlay 3D activation map. Regions of interest (RoI) were identified (FIG. 5) based on a printed human brain atlas w19x and compared to fMRI data sets. In the case of overlays, clusters were included in subsequent statistical analysis. The areas of interest were: BS: brainstem; Tha: thalamus; PFC: prefrontal cortex; POC: postcentral gyrus; PCI: posterior cingulum, insula; NC: nucleus caudatus; Amy: amygdala; Hipp: hippocampus; Put: putamen; DAC: anterior cingulum and NC: nucleus accumbens.

Results

General anamnesis was without pathological findings. High-resolution T1-weighted structural images did not show obvious brain abnormalities or pathologies. There were no adverse effects during the training session and the fMRI experiment. Chosen tVNS parameters ensured that there were no cough reflexes as occasionally reported in the literature as a result of vagus nerve irritations w12x.

Psychophysics

The evaluation of the psychophysiological parameters blood pressure, heart rate and laser Doppler flow showed no significant changes during training session (t-test). After the stimulation, all subjects reported a relaxed yet focussed condition.

Cortical and Subcortical Activations

Figure 6:
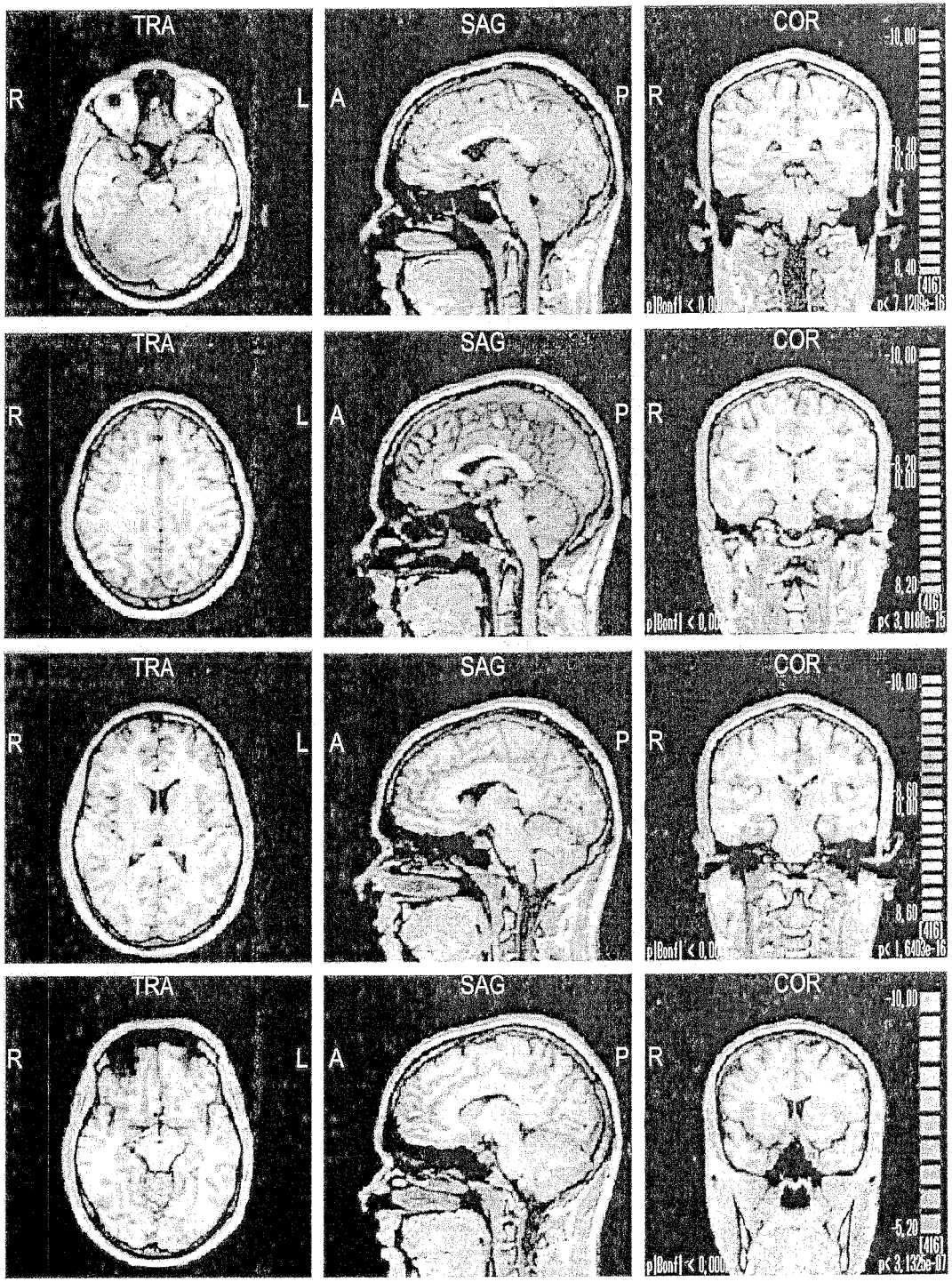

The main results are presented in FIG. 6 and Table 1. In the tVNS_BASELINE comparison, significant areas of activation were detected in the brainstem, more precisely the left locus coeruleus, the thalamus (left4right), the left prefrontal cortex, right and left postcentral gyrus, the left posterior cingulated gyrus and the left insula. Deactivations were found in the right nucleus accumbens and the right cerebellar hemisphere.

In FIG. 6 functional MRI results of the GLM multistudy in a merged display pattern of activations and deactivations. The left row shows axial slices, the middle row different sagittal slices and the right row coronal slices with activated areas in the GLM multistudy. The fourth horizontal row shows deactivations found in the GLM multistudy in axial and sagittal views.

Discussion

The mode of action of VNS is still poorly understood. BOLD fMRI has been studied previously in patients with either treatment resistant depression or epilepsia using the NCP_w2, 16, 17, 21, 23, 24, 31x. We have reviewed recent fMRI/VNS studies (Table 2) and the field is very inconsistent due to missing standardisations in the methods and diverse experimental designs. Nevertheless, there is some agreement across the studies regarding neuroanatomical structures involved in processing VNS signal. Recently, Kraus et al. w13x reported BOLD fMRI deactivations of limbic and temporal brain structures using non-invasive tVNS techniques in healthy subjects. The authors proposed that tVNSs applied to the inner side of the tragus travel along the ramus auricularis nervi vagi towards the brainstem where the signals are processed. However, Kraus et al. w13x could not show brainstem activations that are considered as mandatory for further subcortical and cortical activities. Choosing more specific parameter settings and impulses suitable for parasympathetic nerve system activation (see above), our study showed a more robust activation in the left locus coeruleus (LC), a brainstem nucleus that has recently been related to clinical depression w1x. The LC is the major location of norepinephrine in the brain and some antidepressants are believed to act in this area as norepinephrine reuptake inhibitors. Furthermore, the LC has been studied in relation to VNS. In an experimental animal study, Groves et al. w9x demonstrated direct neuronal responses from the LC following acute challenge of VNS and outlined a pre-eminent impact of the LC for VNS. Krahl et al. w15x showed that lesioning the LC in rats minimises VNS-induced seizure suppression. The projections of the LC are far, e.g., within the brainstem, to the cerebellum, the thalamus and the hypothalamus, the amygdala and the cortex. The LC receives a constant and excitatory input from the prefrontal cortex, an area responsible for executive functions, such as determining good and bad or social control. Interestingly, our study has shown a significant activation of the prefrontal cortex during acute tVNS. Morphometric w26x and functional imaging data w5x have outlined that functional anatomical abnormalities can be related to the onset of depressive disorders. Depressed patients suffer from decreases in cortical thickness, neuronal sizes and area volume. The thalamus is believed to relay information selectively to various parts of the cortex. It also plays an important role in regulating states of sleep and is involved in consciousness. Using tVNS, we produced a bilateral (left4right) activation of this area. We identified the left posterior cingulated gyrus, a part of the limbic system, as another activated brain area. Functional imaging studies consistently found that emotional stimuli activate the posterior cingulate cortex w18x. This region may mediate interactions of emotional and memory-related processes. Moreover, we observed significant deactivations in the right nucleus accumbens (NAc). This nucleus is thought to play an important role by acting as a "motivation relay" between the limbic system and systems involved in motor controls. Furthermore, it seems to be deeply involved in reward, pleasure and addiction generation processes. The NAc has recently been studied in relation to therapy refractory depression. Schlaepfer et al. w30x used deep brain stimulation to stimulate this nucleus along with ventral striatum areas. Their findings, in three patients with refractory depression, suggest that stimulating the NAc might be a new promising approach for treating refractory depressive conditions.

Conclusion

Many studies have revealed that VNS clearly has effects on the brain. As there is some agreement with reviewed fMRI studies on VNS and our results concerning neuroanatomical structures involved in processing VNS signals, our device and parameter settings are feasible and suitable for future scientific tVNS procedures. Our device and the parameters can activate cortical as well as subcortical brain areas including the brainstem. Current state-of-the-art technologies for therapy and diagnosis involve clinical infrastructure (e.g., for imaging) or require surgical interventions. Due to the consistency of our results with traditional VNS, we suggest that this non-invasive tVNS of the ramus auricularis nervi vagi at the left tragus would open new promising applications to diagnose and treat neuropsychiatric conditions, such as treatment resistant depressions or epilepsy.

Figure 7:
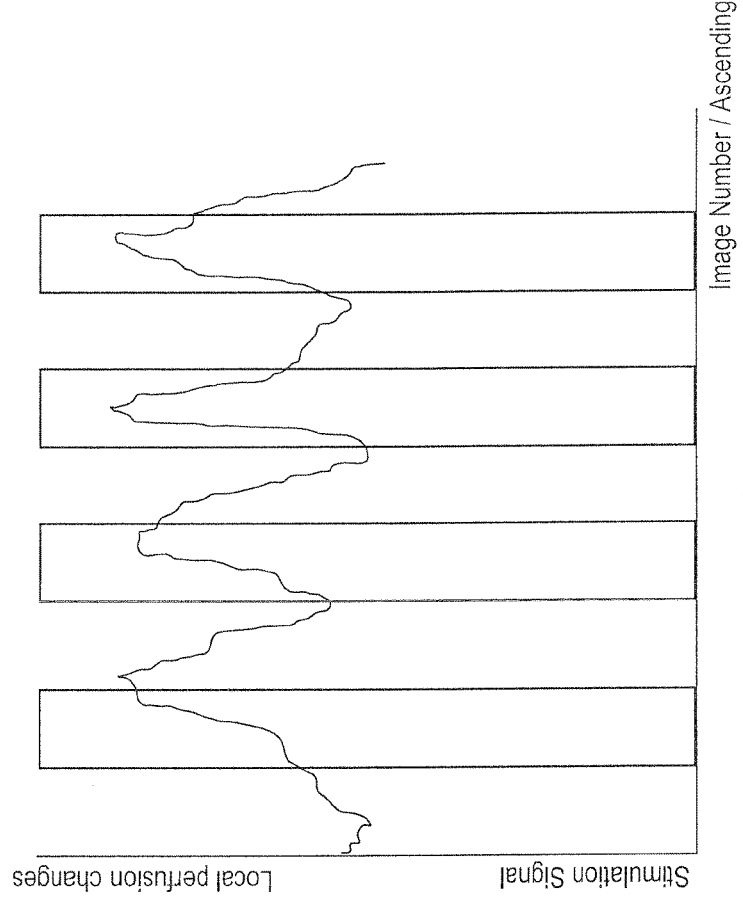
FIG. 7 is a diagram of the neural activity.

FIG. 7 is a schematic showing the signal time course of the focused region of interest in a brainstem nucleus (Locus coeruleus). In this example, the ramus auricularis nervi vagi was stimulated in the left outer ear canal and local perfusion changes were assessed using a classical block design with 4 times stimulation of 30 sec and 5 resting periods each of 60 sec. Neural activity is related to such perfusion changes and changes of the oxy-hemoglobin-to-desoxy-hemoglobin relation. The measurement was performed by using functional magnetic resonance imaging.

Figure 8:
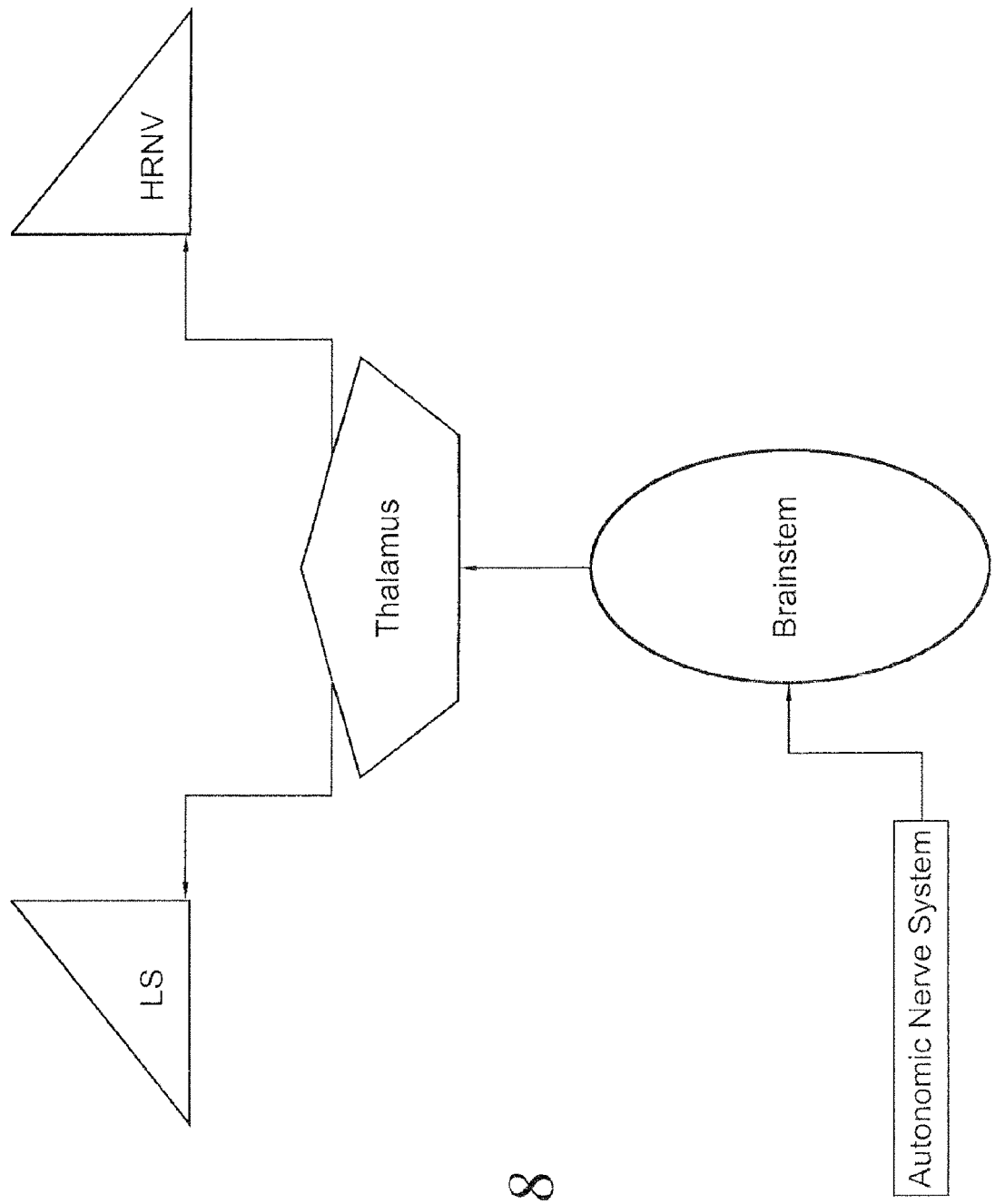
FIGS. 8 and 9 are functional diagrams.

FIG. 8 is a schematic of the neural pathway following electrical stimulation of neural tissue in accordance with preferred embodiment, initiated at a vertebrate's autonomic nerve and followed by propagating action potentials in brainstem, thalamus and higher relay nuclei (in this example of the vagus nerve) or limbic system nuclei.

Figure 9:
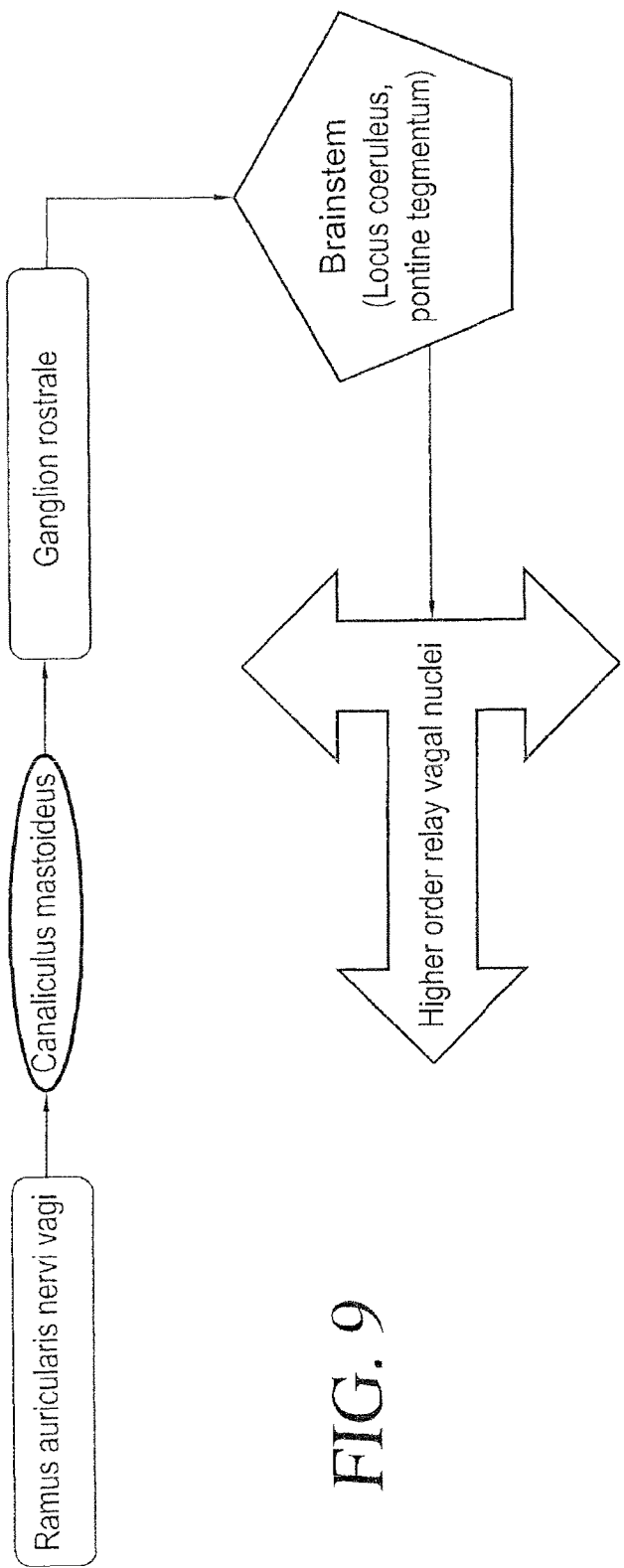

FIG. 9 shows an alternate preferred embodiment wherein transcutaneous vagus nerve stimulation is applied at the ramus auricularis nervi vagi and propagating action potential follow the shown pathway.

TABLE 1

Descriptions of evaluated regions of the brain
Characterisation of tVNS induced cerebral activations and deactivations

| Brain region | Event | Side |
| --- | --- | --- |
| Brainstem (including locus coeruleus) | ↑ | Left |
| Thalamus | ↑ | Left >> Right |
| Hypothalamus | | |
| Putamen | | |
| Nucleus caudatus | | |
| Orbitofrontal cortex | | |
| Prefrontal cortex | ↑ | Left |
| Precentral gyrus | | |
| Postcentral gyrus | ↑ | Bilateral |
| Anterior cingulate gyrus | | |
| Posterior cingulate gyrus | ↑ | Left |
| Insula | ↑ | Left |
| Amygdala | | |
| Hippocampus | | |
| Parahippocampus | | |
| Nucleus accumbens | ↓ | Left |
| Parietal lobe | | |
| Occipital lobe | | |
| Cerebellar hemisphere | ↓ | Left |

A positive correlation in the GLM multistudy is displayed in the column "Event" with a ↑ and a negative BOLD contrast with a ↓. The column "Side" indicates the ipsi (=left), contralateral (=right) or bilateral activated cortical area. Activation in the left thalamus was significantly higher than the right thalamus.

TABLE 2

Summary of the current literature of fMRI studies of vagus nerve stimulation (VNS).
VNS Induced cerebral activity alterations In various fMRI studies

| Struture | Bohning et al. (2001)*** [ref.]*** | Lomarev et al. (2002) [17] | Sucholeiki et al. (2002)*** [ref.]*** | Narayanan et al. (2002)*** [ref.]*** Condition | Liu et al. (2003)*** [ref.]*** | Mu et al. (2004)*** [ref.]*** | Nahas et al. (2007)*** [ref.]*** |
| --- | --- | --- | --- | --- | --- | --- | --- |
| | Treatment-resistant depression | Treatment-resistant depression | Intractable partial seizure | Medically refractory epilepsy | Complex partial seizure | Treatment-resistant depression | Treatment-resistant depression |
| Brainstem | | | | | | ↓lf | |
| Thalamus | | | | ↑bl | | | |
| Hypothalamus | ↑lf | ↑lf | | | | | |
| Cerebellar hemisphere | | | | | | | ↓bl |
| Frontal lobe | | | ↑bl | | | | |
| Prefrontal cortex | | | | | | ↑bl | |
| Superior frontal gyrus | | | | | | | |
| Cingulate gyrus | | | | | ↓bl | ↓ | ↓rg |
| Orbitofrontal gyrus | ↑bl | ↑bl | | | | ↑bl | |
| Postcentral gyrus | | | ↑rg | ↑lf | | | ↑lf |
| Entorhinal gyrus | | | | | | | |
| Temporal lobe | ↑lf | ↑lf | | ↑rg | ↑lf | ↑rg | ↑bl |
| Insula | | | | ↑bl | ↑ | ↑lf | |
| Amygdala | ↑lf | ↑lf | | | ↑ | | |
| Hippocampus | | | | | ↑ | | |
| Parahippocampal gyrus | | | | | | | |
| Nucleus accumbens | | | | | | | |
| Parietal lobe | ↑bl | ↑bl | | | | | |
| Occipital lobe | ↑bl | ↑bl | | ↑lf | | | |
| Putamen | | | | | | ↑lf | |

Remarks

Active VNS group

Depending on the stimulation and scanning protocols, different brain areas are found to be involved. There is some agreement across the studies regarding neuroanatomical structures involved in processing VNS signal.

The invention claimed is:

1. A method for modulation, augmentation and/or stimulation of neural tissue and/or neural tissue related functionality, comprising:
   attaching to the skin of the ear of a patient an acrylic electrode array housing including a sterling silver stimulation electrode and a reference electrode connected with carbon fibre wires to a stand-alone electrical nerve stimulator;
   applying electrical stimuli transdermally at the pinna, wherein a monophasic-modified rectangle impulse with a pulse width of 250 ms, electrical current amplitude between 4 mA and 8 mA stimulation frequency of 25 Hz is used;
   wherein the electrical stimuli applied transdermally at the pinna stimulate the Ramus auricularis Nervi vagi,-neural tissue and/or neural tissue related functionality, and trigger and/or influence neural activity related local perfusion changes;
   performing a BOLD functional MRI session.

2. The method according to claim 1, wherein said stimuli are supplied to at least one means of stimulating neural tissue and/or neural tissue related functionality.

3. The method according to claim 2, wherein said at least one means of stimulating neural tissue and/or neural tissue related functionality is positioned in contact with or proximate to said neural tissue or neural tissue related functionality.

4. The method according to claim 1, wherein said stimuli directly or indirectly interact with a proximate axonal nerve system related target.

5. The method according to claim 1, wherein said stimuli generate local neurophysiological, neurovascular, neuroendocrine and/or neurobiochemical response.

6. The method according to claim 1, wherein said stimuli trigger effects in the brainstem, subcortical and/or cortical areas.

7. The method according to claim 1, wherein said stimuli enhance the performance of neuronal structures and related pathways in vertebrates and/or improve cognitive and emotional abilities and/or alleviate and/or heal neurological and/or neuropsychiatric disorders and/or symptoms resulting from underlying causes.

8. The method according to claim 2, wherein said at least one means of stimulating neural tissue and/or neural tissue related functionality is positioned in contact with or proximate to a nerve of a vertebrate, wherein said nerve comprises parasympathetic and/or sympathetic fibers the Nervus vagus, the Ramus auricuiaris Nervi vagi, and/or a trigeminal nerve.

9. The method according to claim 8, wherein said stimulation generates unidirectionally propagating action potentials.

10. The method according to claim 8, wherein said parasympathetic nerve fibers comprise afferent and/or efferent fibers.

11. The method according to claim 2, wherein said means of stimulating neural tissue and/or neural tissue rotated functionality comprises at least one stimulation electrode.

12. The method according to claim 7, wherein a stimulus amplitude and a stimulus frequency can be modulated and wherein a stimulation pulse comprises at least one of a plateau pulse width of adjustable duration, a rising and decaying trailing phase of adjustable duration and a charge recovery phase of adjustable duration.

13. The method according to claim 1, wherein said stimulation achieves a positive blood oxygenation level-dependent responses in the central nerve system and/or the brain of a vertebrate, wherein said responses take place in the left Locus coeruleus and/or the pontine tegrnenturn and/or the thalamus (left>right) and/or anterior and medial thalamic nuclei and/or the Hippocampus and/or Nucleus paraventricularis and/or the posterior part of the putamen and/or the left prefrontal and/or superior-frontal cortex and/or bilateral postcentral gyrus and/or the left posterior cingulated gyrus and/or the left insula and/or Nucleus accumbens and/or the right cerebellar hemisphere.

14. A method for the treatment of neurological and/or neuropsychiatric disorder and/or symptoms resulting from underlying cause selected from the group consisting of Alzheimer disease, Parkinson disease, Tremor, major depression, bipolar disorders, anxiety, eating disorders, sleep disorders, pain, tinnitus, cardio-vascular disorders, artrial fibrillation, epilepsy, schizophrenia, addictive disorders, dementia, attention deficit disorders, premenstrual syndrome, obesity, spasticity, Tourette syndrome, dystonia, neurogenic and psychogenic bladder disorders, neurogenic and psychogenic defecation disorders, neurogenic and psychogenic sexual disorders, obsessive compulsive disorders with the method according to claim 1.

15. A method for enhancing cognitive and/or emotional abilities according to claim 1.

16. A method for the enhancement of productivity, attention, learning, concentration, awareness, vigilance, tranquillization, sedation, emotional assessment, valuation, emotional intelligence, decisive abilities, retentiveness and/or conversation according to claim 1.

17. The method of claim 1 for generating blood oxygenation level-dependent responses in higher order relay nuclei of vagal afferent pathways, wherein the method comprises one or more of the following steps:
   generating propagating action potentials of the Ramus auricularis Nervi vagi by means of stimulation;
   transmitting said propagating action potentials to pass through the Canaliculus mastoideus;
   transmitting said propagating action potentials to pass the Ganglion rostrate;
   transmitting said propagating action potentials to generate blood oxygenation level-dependent responses in the brainstem; and
   transmitting said propagating action potentials to generate blood oxygenation level-dependent responses in the Thalamus.

18. The method according to claim 17, wherein said method for generating blood oxygenation level-dependent responses in higher order relay nuclei of vagal afferent pathways comprises means of influencing propagation of said action potentials towards subcortical and cortical brain areas associated with vagal and limbic pathways.

19. The method according to claim 1, wherein said stimuli are electrical stimuli applied transdermally at the tragus.

* * * * *